United States Patent [19]
Tam

[11] Patent Number: 5,461,650
[45] Date of Patent: Oct. 24, 1995

[54] METHOD AND SYSTEM FOR PRE-PROCESSING CONE BEAM DATA FOR RECONSTRUCTING FREE OF INTERPOLATION-INDUCED ARTIFACTS A THREE DIMENSIONAL COMPUTERIZED TOMOGRAPHY IMAGE

[75] Inventor: Kwok C. Tam, Schenectady, N.Y.

[73] Assignee: General Electric Company, Schenectady, N.Y.

[21] Appl. No.: 137,543

[22] Filed: Oct. 18, 1993

[51] Int. Cl.$^6$ ............................ A61B 6/03; G01N 23/083
[52] U.S. Cl. ..................... 378/4; 378/901; 364/413.15; 364/413.19
[58] Field of Search ................ 364/413.15, 413.16, 364/413.17, 413.18, 413.19, 413.20; 378/901, 15, 8, 4

[56] References Cited

U.S. PATENT DOCUMENTS

| | | | |
|---|---|---|---|
| 5,257,183 | 10/1993 | Tam | 364/413.19 |
| 5,319,693 | 6/1994 | Eberhard et al. | 378/19 |
| 5,355,309 | 10/1994 | Eberhard et al. | 364/413.15 |
| 5,383,119 | 1/1995 | Tam | 364/413.19 |
| 5,390,111 | 2/1995 | Tam | 364/413.14 |
| 5,390,226 | 2/1995 | Tam | 378/19 |

OTHER PUBLICATIONS

"Cone–beam Tomography: Recent Advances and a Tutorial Review", Bruce D. Smith, Optical Engineering–May 1990, vol. 29. No. 5–pp. 524–534.
"Image Reconstruction from Cone–Beam Projections: Necessary and Sufficient Conditions and Reconstruction Methods", Bruce D. Smith, IEEE Transactions on Medical Imaging, vol. MI–4, No. 1, Mar. 1985, pp. 14–25.

*Primary Examiner*—David P. Porta
*Assistant Examiner*—David Vernon Bruce
*Attorney, Agent, or Firm*—Enrique J. Mora; Marvin Snyder

[57] ABSTRACT

Techniques and system for pre-processing cone beam projection data for reconstructing substantially free of interpolation-induced artifacts a three-dimensional computerized tomography (CT) image of a portion of an object are provided. Such techniques include identifying first, second and third regions on a surface array detector such that only cone beam projection data acquired in the identified regions is retained for subsequent processing. The identified regions cooperate to eliminate interpolation effects upon lines of integration situated relatively close to boundaries on the array detector and thus allow for reconstructing the substantially free of interpolation-induced artifacts CT image.

22 Claims, 4 Drawing Sheets

METHOD AND SYSTEM FOR PRE-PROCESSING CONE BEAM DATA FOR RECONSTRUCTING FREE OF INTERPOLATION-INDUCED ARTIFACTS A THREE DIMENSIONAL COMPUTERIZED TOMOGRAPHY IMAGE

CROSS REFERENCE TO RELATED APPLICATIONS

This application is related to the following commonly assigned U.S. patent applications, the entire disclosures of which are hereby expressly incorporated by reference:

Application Ser. No. 07/725,142 now U.S. Pat. No. 5,383,119, by Kwok C. Tam entitled "METHOD AND APPARATUS FOR ACQUIRING COMPLETE RADON DATA FOR EXACTLY RECONSTRUCTING A THREE DIMENSIONAL COMPUTERIZED TOMOGRAPHY IMAGE OF A PORTION OF AN OBJECT IRRADIATED BY A CONE BEAM SOURCE"; and Application Ser. No. 07/908,114, now U.S. Pat. No. 5,390,226 by Kwok C. Tam entitled "METHOD AND APPARATUS FOR PREPROCESSING CONE BEAM PROJECTION DATA FOR EXACT THREE DIMENSIONAL COMPUTER TOMOGRAPHIC IMAGE RECONSTRUCTION OF A PORTION OF AN OBJECT".

BACKGROUND OF THE INVENTION

The present invention relates generally to three-dimensional (3D) computerized tomography (CT) and, more particularly, the present invention relates to a method and system for pre-processing cone beam projection data for reconstructing substantially free of interpolation-induced artifacts a 3D image of a portion of an object.

Commonly assigned patent application Ser. No. 07/725,142 by Kwok C. Tam discloses method and apparatus for imaging a portion of an object irradiated in a field of view of a cone beam source such as a cone beam x-ray source or other suitable point source of radiant or electromagnetic energy. A portion of interest undergoing imaging inspection may be a preselected portion of an object which is wholly engulfed within the field of view of the cone beam source. Alternatively, the portion of interest to be imaged may be limited to only that portion of the object which fits within the field of view of the cone beam source, as is typically the case when the entire object is too large to be wholly irradiated thereby. In either case, the portion of interest can be rotationally scanned by the x-ray cone beam source at respective upper and lower extents thereof along a scan trajectory having upper and lower scan paths which serve to bound the portion of interest. To ensure that a complete Radon data set is acquired for exact image reconstruction, the upper and lower scan paths are connected by a connecting scan path to effectively provide a complete scan trajectory. Cone beam projection data is detected by a suitable surface array radiation detector wherein the source and array detector are mutually fixed with respect to one another so as to scan the portion of interest to acquire cone beam projection data for a plurality of source positions along the scan trajectory.

To insure exact image reconstruction, cone beam projection data is generally acquired using a technique which fills Radon space over a region of support in Radon space corresponding to the field of view occupied by the portion of interest of the object in real space. Such filling technique is chosen to provide sufficient Radon data to completely and exactly reconstruct a 3D CT image by a process of inverse Radon transformation. Preferably, at least a requisite core number of necessary data points in Radon space can be selectively retained for subsequent processing so as to exactly image the portion of interest. A 3D CT cone beam reconstructed image obtained by inverse Radon transformation utilizes a mathematical point by point inversion technique. The Radon inversion technique is inherently a computationally intensive technique which becomes unduly burdened by tracking Radon data points which either do not contribute or redundantly contribute to reconstruction of a 3D image of the portion of interest. Typically, either each Radon data point collected throughout Radon space is indiscriminately retained for point by point inversion processing, or a truncated subset of Radon data points, representing only cone beams which actually pass through the object, is selectively retained for point by point inversion processing. Truncation boundaries in Radon space are typically identified by the use of a projection and/or intersection operations which are easier to apply than direct point by point mathematical manipulations.

In a typical 3D CT reconstruction by Radon inversion, suitable integrals such as planar integrals are calculated and organized as discrete data points in Radon space. The planar integrals are based upon cone beam projection data measured by the detector. Radon data points are organized onto an arbitrary set of planes in Radon space, wherein each plane of integration is used to calculate a Radon derivative corresponding to a single data point in Radon space. These discretely organized Radon data points are typically partitioned and selectively retained or discarded according to whether or not corresponding planes of integration intersect the portion of interest of the object. By its mathematical nature, Radon space is a collection of discrete Radon data points each corresponding to a plane of integration, e.g., a planar integral. For each integration plane that intersects the portion of interest, the corresponding computation of a Radon derivative, i.e., a Radon data point, depends upon the manner in which that plane intersects with the portion of interest. Thus, the adequacy of filling the region of support in Radon space is generally assessed by first suitably partitioning those integration planes which contribute to data points in Radon space.

Typical image reconstruction of the portion of interest generally requires the following procedure: 1) identifying a plurality of suitable integration planes; 2) determining an appropriate angular range of the x-ray cone beam for each contributing source position required to compute the Radon derivative for each identified integration plane; and 3) keeping track of the exact number of source positions that contribute to a particular Radon data point. Commonly assigned patent application Ser. No. 07/908,114 by Kwok C. Tam improves the general approach of patent application Ser. No. 07/725,142 by eliminating such requisite procedure by pre-processing cone beam projection data for image reconstruction in a manner whereby only cone beam projection data acquired within a select region identified on the surface array detector is retained for further processing. Thus, image processing using the foregoing pre-processing conveniently requires fewer operations resulting in saving time, money and computer resources.

The approach of patent application Ser. No. 07/908,114 is illustrated in FIGS. 1a and 1b. FIG. 1a illustrates an object 22 wherein a cylindrical portion 23, for example, is the portion of interest undergoing inspection. This portion is labelled "X" and is bounded by an upper scan path 24, labelled "$C_1$", and a lower scan path 26, labelled "$C_2$", with a predetermined connecting scan path therebetween (not shown). For the sake of illustration and not of limitation, upper and lower scan paths 24 and 26, are herein illustrated as circular paths enclosing the cylindrical portion of interest 23. Consider cone beam source 28 along upper scan path 24, a projection of upper and lower scan paths 24 and 26 onto surface array detector 32 can be characterized by a boundary projection operator "P" operating on scan paths 24 and 26, respectively. The boundary projection operation on the upper scan path can be symbolically represented by $P(C_1)$ and such upper scan path simply projects onto surface array detector 32 as a straight line 34. Similarly, boundary projection operation $P(C_2)$ can be shown to project the lower scan path onto detector 32 as a parabolic curve 36.

As illustrated in FIGS. 1a and 1b, a closed region 44 on surface array detector 32 results upon operation of a mask projection operator M conceptually represented by a suitably identified first region 38 in the square designated as M. Mask projection operator M upon operating on an overall cone beam projection 42 of the object 22 and cooperating with boundary operator P advantageously provides closed region 44 further shown in the square designated as MP(X). Thus, closed region 44 is obtained by taking the intersection of the overall cone beam projection 42 of object 22 with mask operator M (i.e., first region 38) onto surface detector 32 wherein such intersection is bounded by $P(C_1)$ at straight line 34 and $P(C_2)$ at parabolic curve 36. Thus cone beam projection data can be acquired at the array detector for each position along the scan trajectory, retaining only that cone beam projection data acquired within first region 38 for further processing. This manner of pre-processing data amounts to processing only data collected within first region 38 which is herein referred to as a masked cone beam region.

For the sake of explanation, a given exemplary energy cone beam detected at surface array detector 32 within first region 38, can represent, for example, the cone beam emitted from source scan position A, within an angle conveniently chosen to span at least the boundaries or edges defined by projection of upper scan path $C_1$, at straight line 34, and the projection of lower scan path $C_2$, at parabolic curve 36. Thus, it will be appreciated that such exemplary cone beam intersects at least certain predetermined subportion of portion of interest 23 being that the upper and lower scan paths as well as the connecting path cooperate to fully enclose portion of interest 23. Additional source scan positions can provide cone beam projections which are limited to within the masked cone beam region. In essence, such cone beam projections are obtained from cone beams which can be characterized as passing only through portion of interest 23 (labelled as X) without contamination by the rest of object 22, i.e., remaining portions of the object other than portion X. Based upon the above characterization there is no longer a need to distinguish between different categories of integration planes by partitioning those integration planes which contribute to data points in Radon space. Although such otherwise requisite partitioning procedure is therefore eliminated which results in saving time, money and computer resources, certain image artifacts unfortunately can occur.

To obtain cone beam projection data uncontaminated by the rest of object 22, it will be appreciated that cone beam projection data acquired outside first region 38 is set to a zero value, i.e., individual detector elements such as pixel detectors situated outside the masked cone beam region are collectively set to have a respective value of zero. Thus, whenever a line of integration used in calculating Radon data lies relatively close to and generally parallel to the boundaries of first region 38, interpolation-induced artifacts can occur. For instance, such interpolation-induced artifacts typically arise due to the influence of the zero values from the pixel detectors situated outside first region 38. The pixels having zero values, for example, can erroneously reduce the magnitude of interpolated values for similarly situated lines of integration used in calculating Radon data for the portion of interest, and generally result in an image having noticeable interpolation-induced artifacts. (No representation is made or intended that these referenced applications are necessarily prior art to the present application).

OBJECTS AND SUMMARY OF THE INVENTION

Accordingly, it is a general object of the present invention to provide an improved 3D CT imaging technique.

A more specific object of the present invention is to provide for imaging a portion of an object substantially free of interpolation-induced artifacts.

It is another object of the present invention to provide a pre-processing technique for eliminating interpolation effects upon lines of integration situated relatively close and generally parallel to a first region identified for retaining cone beam projection data.

It is yet another object of the present invention to provide a system for eliminating interpolation effects upon lines of integration situated relatively close and generally parallel to a first region identified for retaining cone beam projection data.

The foregoing and other objects and advantages of the present invention which will become more apparent from the following detailed description are realized by a method for preprocessing cone beam projection data for reconstructing substantially free of interpolation-induced artifacts a 3D image of a portion of an object using an inverse Radon transformation. A mutually spaced cone beam irradiating source and a surface array radiation detector are provided in fixed relationship to one another. The object undergoing inspection, for example, is provided between the source and the detector such that at least the portion of the object to be imaged is irradiated by the source. Both the source and detector can be moved relative to the object for scanning around the portion to be imaged along a scan trajectory enclosing upper and lower extents of such portion by respective upper and lower scan paths preferably joined therebetween by a predetermined connecting path.

A first region is identified on the surface array detector as a cone beam projection of the object bounded between respective similar projections of the upper and lower scan paths. Second and third regions are further identified on the detector and are respectively situated about the upper and lower scan path projections. By way of example and not of limitation, the identified second and third regions can be respectively situated adjacent to the upper and lower scan path projections. Further, each respective one of the second and third regions can share a respective mutually intersecting subregion with the first region. In each case each of the second and third identified regions respectively extends sufficiently beyond the first identified region to provide a predetermined additional cone beam projection of the object. Cone beam projection data is acquired at the detector for a plurality of scan positions along the scan trajectory. The cone beam projection data acquired within said first, second and third regions is retained for subsequent processing to reconstruct substantially free of interpolation-induced artifacts a 3D image of the portion using the inverse Radon transformation.

The three-dimensional computerized tomography system according to the present invention includes a suitable radiation cone beam source for irradiating at least a portion of the object to be imaged. A surface array radiation detector is positioned to receive radiation from the source. A scanning device causes relative motion of the source and object such that the source moves along a scan trajectory relative to the portion of the object to be imaged. The scanning device includes means for scanning along upper and lower scan paths respectively enclosing upper and lower extents of the portion of the object and along a connecting path between the upper and lower scan paths. Means for identifying a first region on the surface detector is used to provide a cone beam projection of the object bounded between the upper and lower scan paths. The system further includes means for identifying second and third regions on the surface detector as discussed above. Means for acquiring cone beam projection data with the source at a plurality of positions along the scan trajectory is used to acquire complete cone beam projection data corresponding to the portion of the object to be imaged. Means for retaining the cone beam projection data acquired within the first, second and third regions can be utilized by means for processing such retained data (such as a computer work station and the like) to construct an exact 3D image of the portion of the object substantially free of interpolation-induced artifacts using the Radon inverse transformation. A display can be connected to the computer workstation for displaying such image.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description in conjunction with the accompanying drawings in which like characters represent like parts throughout the drawings, and in which:

DETAILED DESCRIPTION OF THE INVENTION

Figure 1A:
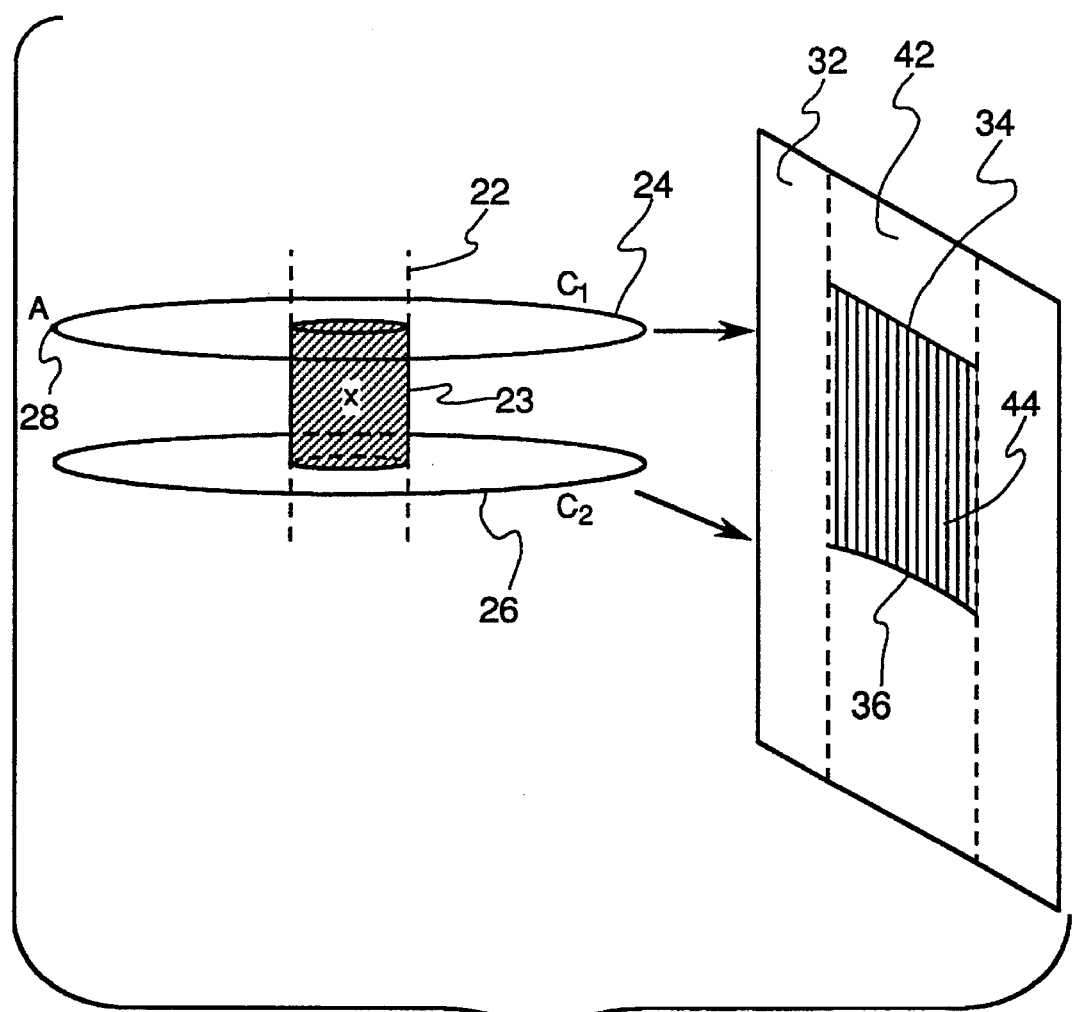
FIGS. 1a and 1b depict an exemplary configuration wherein a cone beam radiation source and a surface array detector scan a portion of an object to be imaged and wherein only data acquired within a first region identified on the array detector is retained for further image processing.
Figure 1B:
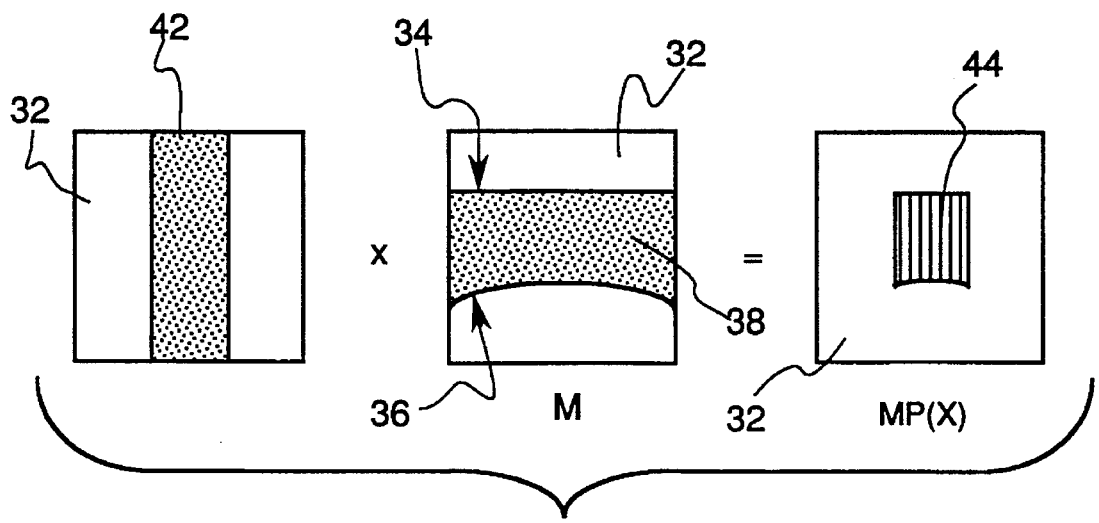

In a typical scanning and data acquisition configuration which employs cone beam geometry, as discussed in the context of FIGS. 1a and 1b in the background section of the present disclosure, the field of view of the source can enclose a portion of the object or workpiece to be imaged. More generally, it will be understood that the object is not necessarily a workpiece or a portion thereof, but may be a human or animal patient or portion thereof which is to be imaged for medical purposes. In either case, a suitable cone beam radiation source 28 and a typical surface array radiation detector 32 cooperate along a defined source scan trajectory in a manner generally well understood by those skilled in the art to provide cone beam projection data. Whether the object is part of a workpiece being inspected for industrial purposes, or a portion of a human or a animal patient being analyzed for medical purposes, the frame of reference which will be generally used in this discussion will be the frame of reference of the object. Thus, the discussion will refer to the trajectory or scan path of source 28. However, it will be understood that the relative motion between source 28 and the object may be accomplished by: moving source 28 while the object remains stationary, moving the object while source 28 is stationary, or by moving both the object and source 28 at the same time. In medical applications where the object is a patient or part of a patient, source 28 is usually moved while the patient is stationary. In industrial applications where the object may be part or all of a workpiece, the workpiece is usually moved while the source 28 is maintained stationary.

As is generally appreciated in the field of three-dimensional computerized tomography (CT), surface array detector 32 which can be conveniently implemented as a planar surface array detector detects cone beam radiation which has passed through at least a portion of the object to be imaged. Usually, and as contemplated by the present invention, the array detector would be fixed relative to source 28, that is, the detector would move relative to the object, but not relative to the source 28. However, the present invention does not necessarily require that the area detector is fixed relative to source 28. The source 28 is preferably an x-ray cone beam radiation source, but could be alternatively a source of neutrons, positrons, or other form of radiation or electromagnetic energy from a point source.

Figure 2:
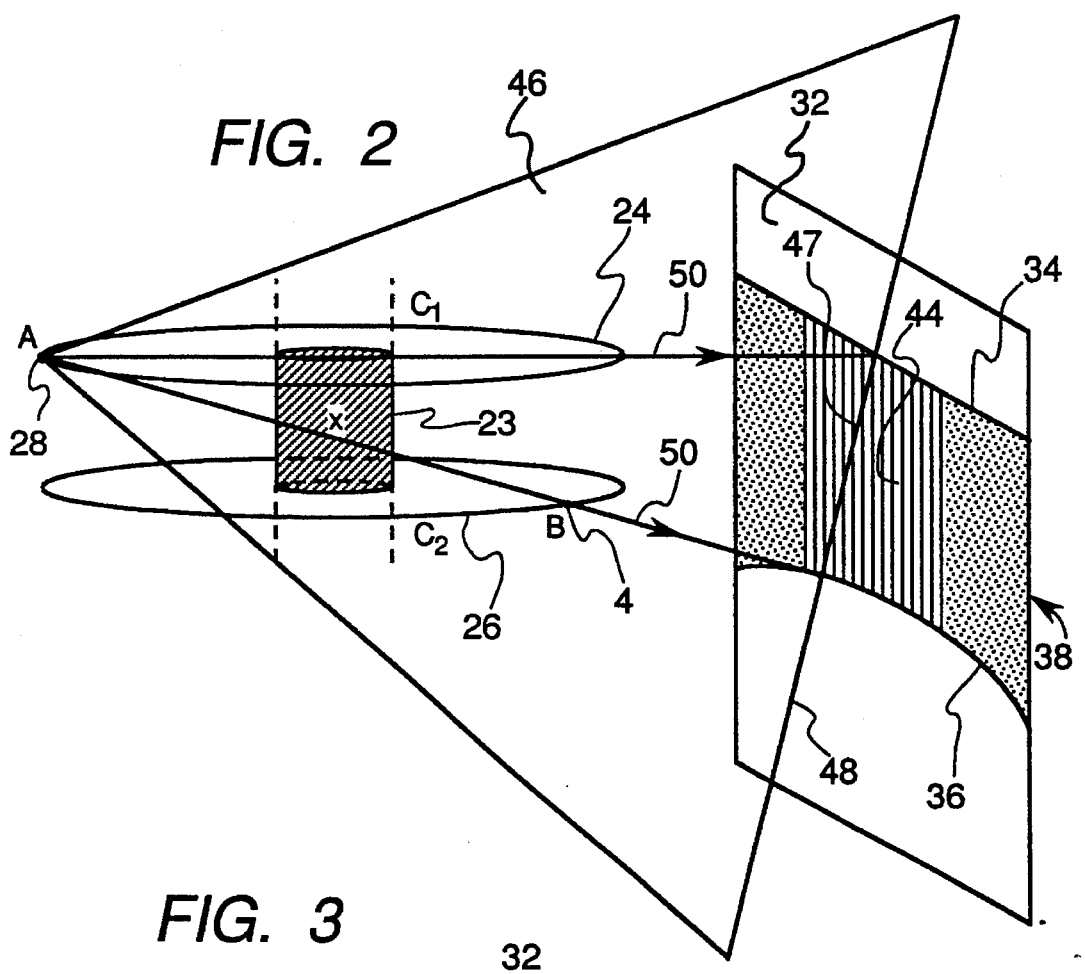
FIG. 2 depicts an exemplary plane for conceptually illustrating a line of integration for obtaining Radon data.

FIG. 2 illustrates that any plane, such as exemplary plane 46, which intersects a given source scan position A, for example, and portion of interest 23, also intersects surface array detector array 32 along a line 48 which extends through first region 38, i.e., the masked cone beam region. The segment of line 48 identified by numeral 47 lying within first region 38, corresponds to x-ray beams emitted from source position A within an angle conveniently chosen to span upper scan path projection 24 and lower scan path projection 26, as previously illustrated in FIG. 1a. This angular range is precisely the same angular range of cone beam data needed to compute a Radon derivative for at least an upper subportion of portion X, such as the upper subportion spanned by exemplary rays 50. Thus, utilizing cone beam data acquired within first region 38, conveniently provides the Radon derivative for at least such upper subportion of portion X. Similarly, source position B can be shown to provide the Radon derivative corresponding to the remaining lower subportion of portion X. Although line segment 47 is shown in FIG. 2 as traversing first region 38 in a generally vertical direction, such line segment could have been shown as traversing first region 38 in a horizontal direction generally parallel to scan path projections 34 and 36. In each case, line segment 47 can conceptually represent a line of integration upon which a suitable integration operation, such as for example a predetermined weighted integration operation, is performed to acquire Radon data which corresponds to the point in Radon space for which the Radon derivative is being calculated.

Figure 3:
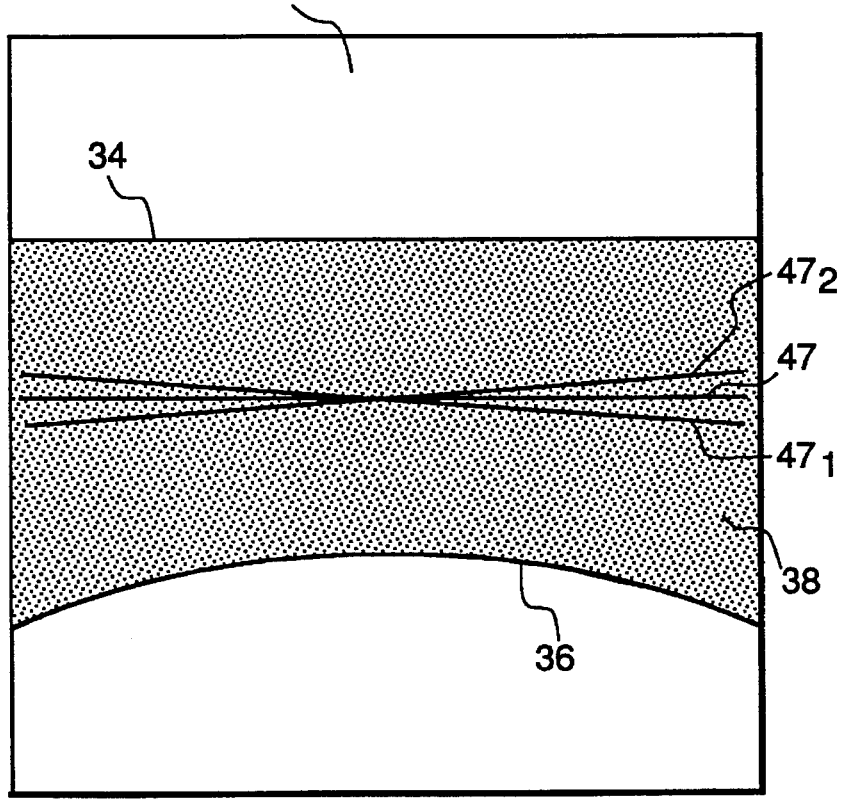
FIG. 3 depicts further details for obtaining Radon data corresponding to a line of integration similar to that illustrated in FIG. 2.

The foregoing line of integration 47 and associated integration operation can be better appreciated with reference to FIG. 3 wherein lines $47_1$ and $47_2$ represent two closely spaced lines bordering line of integration 47 and cooperating to provide the cone beam projection data required to calculate the Radon derivative corresponding to line of integration 47. In known fashion and based upon cone beam projection data acquired on respective detector elements (i.e., pixel detectors) situated along lines $47_1$ and $47_2$, the foregoing weighted integration operation is performed. It will be appreciated by those skilled in the art that cone beam projection data at predetermined discrete points along lines $47_1$ and $47_2$ is typically obtained by known interpolation techniques between neighboring pixel detectors situated in predetermined rows and columns of the array detector 32.

Figure 4B:
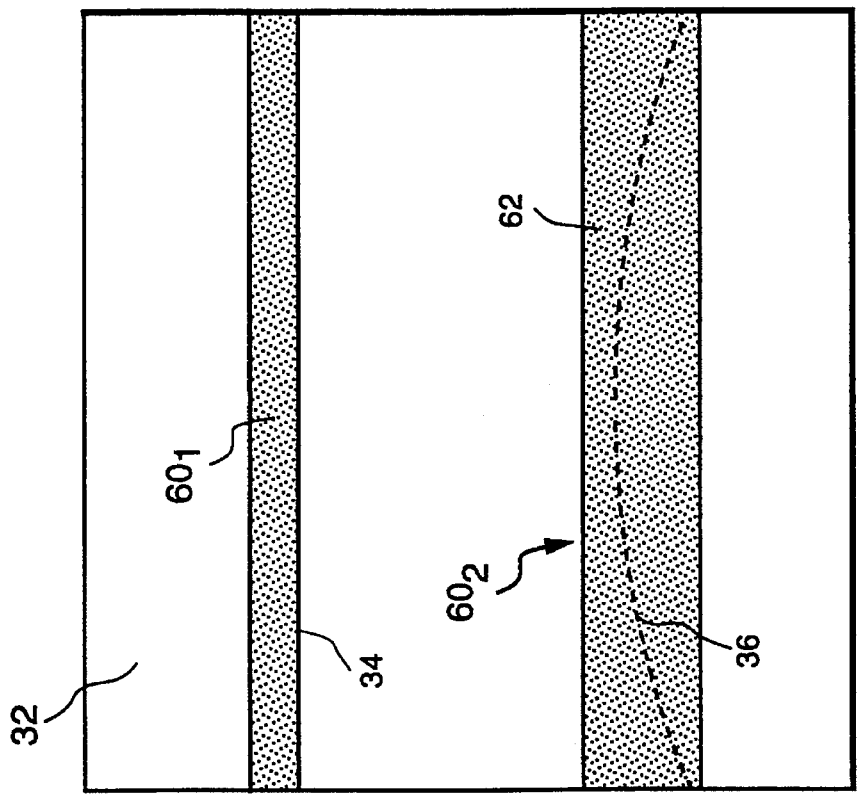
FIGS. 4a and 4b depict exemplary first, second and third regions which are suitably identified to eliminate interpolation-induced artifacts in accordance with the present invention.
Figure 4A:
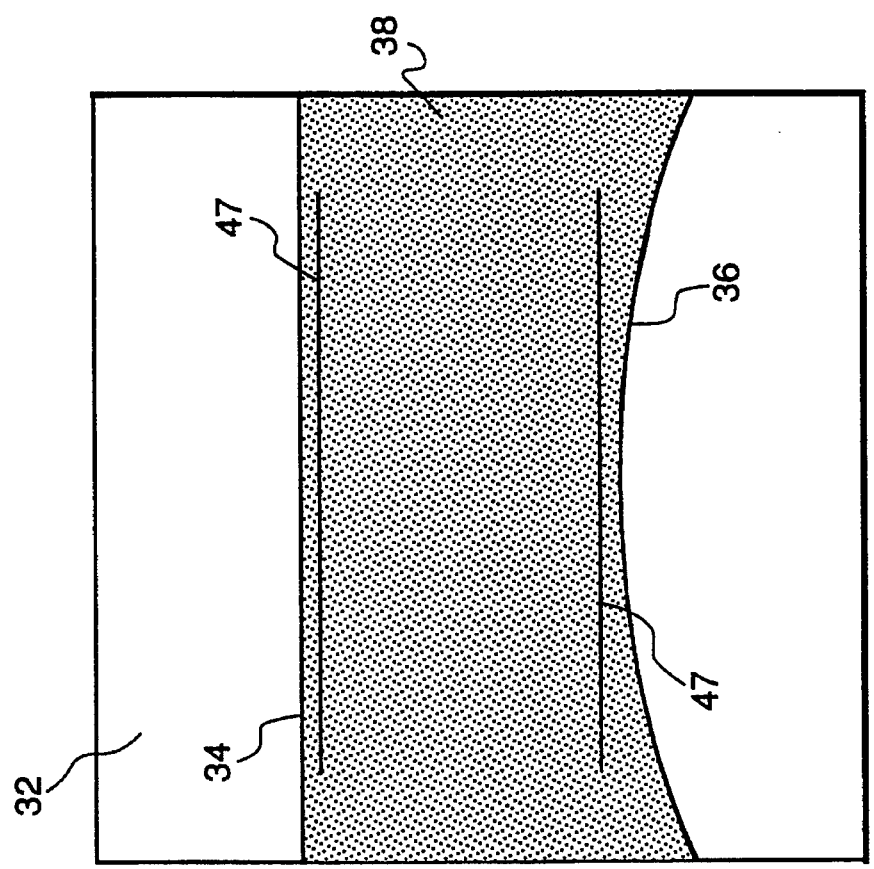

From FIG. 4a it should be appreciated that when the line of integration 47 lies relatively close and generally parallel to respective boundaries of first region 38, such as scan path projections 34 and 36, some of the discrete points along the line of integration are affected by the pixel detectors set to a zero value which lie outside first region 38. Pixel detectors having zero values outside first region 38 can erroneously reduce the magnitude of the interpolated values corresponding to a given discrete point on the line of integration. Such interpolation errors can render the weighted integral operation inaccurate which in turn induces interpolation-induced artifacts in the image for the portion of interest.

In accordance with the present invention, FIG. 4b shows that suitable second and third regions $60_1$ and $60_2$, respectively, can be identified on the surface array detector 32 to provide respective additional cone beam projections of the object. The second and third regions $60_1$ and $60_2$ are respectively situated about the upper and lower scan path projections. For the purpose of explanation and not of limitation, if FIG. 4b were superimposed over FIG. 4a, it should be appreciated that second region $60_1$, for example, can be situated adjacent to the upper scan path projection 34. Again for the purpose of explanation and not of limitation, it should be further appreciated that third region $60_2$, for example, can share a respective mutually intersecting sub-region 62 with first region 38. In each case, each second and third region extends sufficiently beyond first region 38 to respectively provide such additional beam projection of the object. In essence, each second and third region provides a respective guard band beyond first region 38 or on either side along scan path projections 34 and 36 which advantageously operates to retain data by pixel detectors which instead of having a value of zero, have a respective value corresponding to the actual cone beam projection of the object. Thus, in accordance with the present invention interpolated values for an integration line situated relatively close to a given boundary of first region 38 are not affected by pixel detectors set to have a zero value. The illustrated configurations shown for the second and third regions $60_1$ and $60_2$ are merely exemplary being that other configurations can be effectively used in accordance with the teachings of the present invention so long as the second and third regions extend sufficiently beyond first region 38 to avoid the influence of zero values from the pixel detectors situated outside first region 38 and in the vicinity of respective boundaries thereof such as respective boundaries 34 and 36. Cone beam projection data can thus be conveniently acquired at detector 32 for a plurality of scan positions along the scan trajectory. Further, retaining cone beam projection data acquired in such first, second and third regions, insures that subsequent processing of such retained data results in reconstructing a 3D image of the portion of the object which is substantially free of interpolation-induced artifacts. The image reconstruction being implemented, for example, by using the inverse Radon transformation.

Techniques for allowing computation of Radon data from cone beam projection data can be performed in known fashion and need not be described in detail. Briefly, most image reconstruction procedures in x-ray CT are based on the Radon inversion process, in which the image of an object is reconstructed from the totality of the Radon transform of the object. The Radon transform of a 3D object consists of planar integrals. The cone beam projection data, however, is not directly compatible with image reconstruction through inverse Radon transformation, which requires the use of planar integrals of the object as input. Consequently, image reconstruction by inversion from cone beam scanning data generally comprises two steps. A first step is to convert the cone beam data to planar integrals. A second step is then to perform an inverse Radon transform on the planar integrals to obtain the image.

The first step is described by the present inventor's allowed application Ser. No. 07/631,815, filed Dec. 21, 1990, entitled "METHOD AND APPARATUS FOR CONVERTING CONE BEAM X-RAY PROJECTION DATA TO PLANAR INTEGRALS AND RECONSTRUCTING A THREE-DIMENSIONAL COMPUTERIZED TOMOGRAPH (CT) IMAGE OF AN OBJECT", assigned to the assignee of the present application and hereby incorporated by reference. A technique for performing an inverse Radon transform on planar integrals to obtain an image is described in the present inventor's prior patent application Ser. No. 07/631,818, now abandoned, filed Dec. 21, 1990, entitled "PARALLEL PROCESSING METHOD AND APPARATUS FOR RECONSTRUCTING A THREE-DIMENSIONAL COMPUTERIZED TOMOGRAPHY (CT) IMAGE OF AN OBJECT FROM CONE BEAM PROJECTION DATA OR FROM PLANAR INTEGRALS", assigned to the assignee of the present application, and hereby incorporated by reference. Thus, those two prior incorporated by reference U.S. patent applications describe techniques which may be used for three-dimensional image reconstruction by Radon inversion from cone beam projection data.

Figure 5:
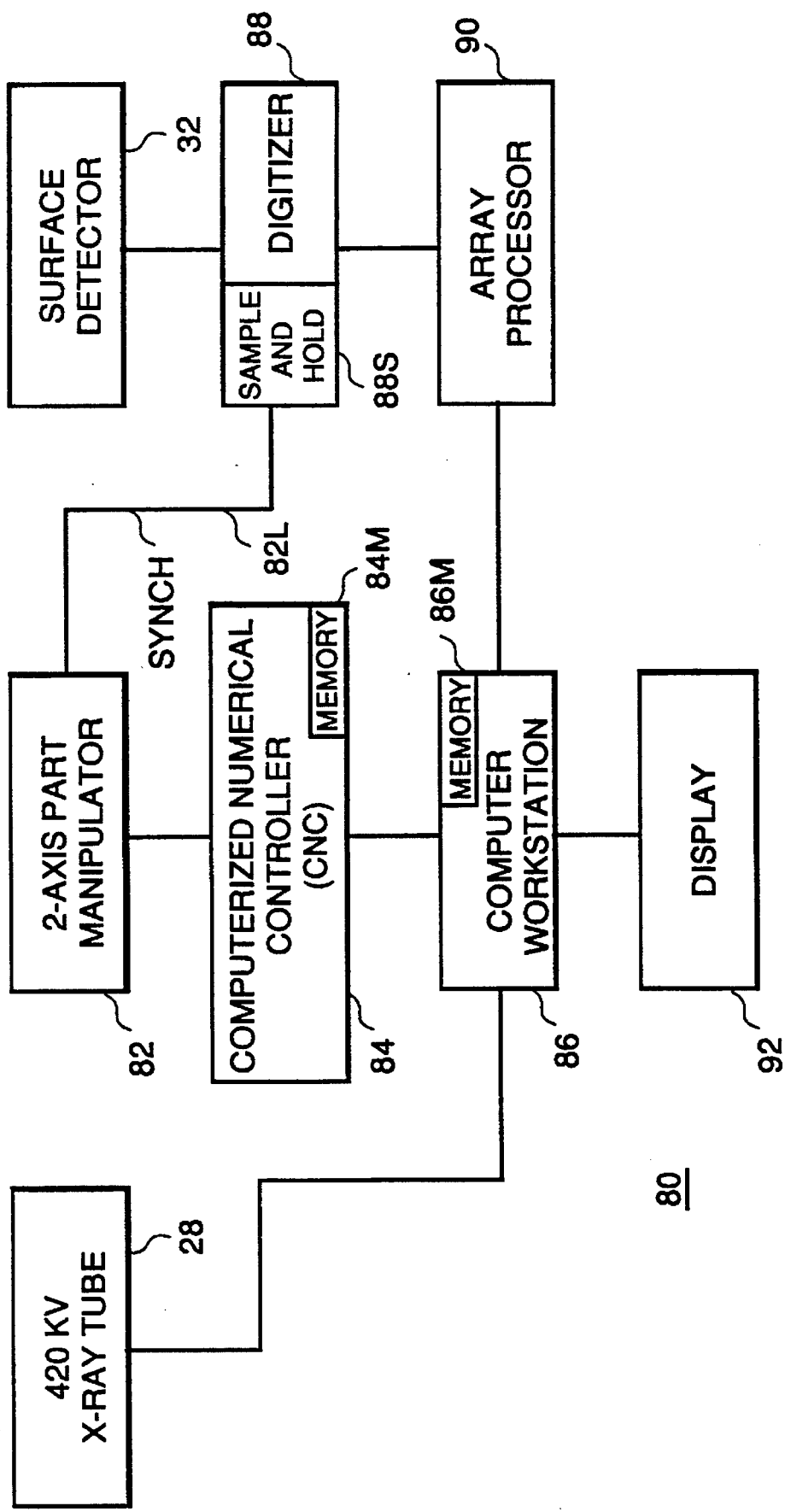
FIG. 5 is a simplified block diagram illustrating components of the system of the present invention.

Turning now to FIG. 5, a system 80 according to the present invention will be discussed. The system includes the cone beam radiation source 28 and surface array detector 32. Although the source 28 is shown as an x-ray tube, the cone beam radiation source 28 could alternatively provide neutrons, positrons, or other forms of radiation or electromagnetic energy from a point source. Alternatively, other forms of imaging energy might be used.

A manipulator 82, which may be a two-axis part manipulator, is an example of a scanning device used to provide the relative scanning movement between the portion (not shown in FIG. 5) which is to be imaged and the source 28. Although the manipulator 82 is designed to move the object, the manipulator 82 might alternatively move the source 28.

The manipulator 82 is controlled by a known computerized numerical controller (CNC) 84, which may, for example, be of a type made by Aerotech. The controller 84 may include a memory 84M having suitable data defining the scan trajectory path in known fashion. Alternatively, and also using well known techniques, a memory 86M of a computer work station 86, which is connected to the controller 84, may have the data which defines movements of the manipulator 82 and therefore defines the trajectory of the type previously discussed with respect to FIGS. 1a and 2 of the present application. The computer work station 86 may be a work station made by Sun, although other computer work stations and possibly even personal computers might be used in place of the work station. The computer work station controls the other components of the system 80 in known fashion. Further, the computer work station can conveniently provide stored within memory 86M a program having a module for identifying the first, second and third regions discussed in the context in FIGS. 2, 4a and 4b. Memory 86M or memory 84M can provide convenient means for retaining cone beam projection data acquired within the first, second and third regions.

Connected to the surface array detector 32 is a digitizer 88 which operates in known fashion to convert analog signals from the array detector into digital signals representative of the image of the portion undergoing inspection. The digitizer 88 may include sample and hold circuits 88S operating in response to a synch signal on line 82L in known fashion. Thus, digitizer 88 provides suitable means for acquiring cone beam projection data with the source at a plurality of positions along the scan trajectory.

The digitized values corresponding to the detected cone beam radiation, that is, cone beam projection data from the detector elements, i.e., pixel detectors within detector 32, are supplied from the digitizer 88 to a data array processor 90. The array processor 90, which may be of a known commercially available type such as a Meiko M40, provides the necessary signal processing for the signals coming from the digitizer 88. The array processor 90 may perform the necessary image reconstruction and processing such that a display might be connected directly to the array processor to display the images from the CT scan. However, in the arrangement shown in FIG. 5, the image data from array processor 90 is supplied to computer work station 86 and the computer work station 86 in turn supplies the data, with or without further processing, to a display 92 which displays the CT images. The computer 86 or, more preferably, array processor 90 reconstructs an image from a complete data set generated from combining cone beam data corresponding to respective subportions of the portion to be imaged such as suitable upper and lower subportions, for example. Thus, either computer workstation 86 or array processor 90 provide suitable means for processing the retained cone beam data combined to generate the complete data set which can be exactly reconstructed into an image of the portion of interest.

Upon suitable operation of the manipulator 82, the system 80 of FIG. 5 may be used to realize techniques described in the context of FIGS. 1a and 2. That is, the manipulator 82 may simply move the object (not shown in FIG. 5) in a scanning movement relative to source 28 along the scan trajectory having upper or lower scan paths. It will be appreciated that the scanning movement along the scanning trajectory can be either step-wise or continuous scan depending on the particular implementation.

Stored within memory 84M or memory 86M would be a program having a module which controls manipulator 82 and/or possibly a second manipulator (not shown) in order to position the object, source, and array detector in suitable scanning positions. Another module of the program, most likely stored in memory 86M, would organize the cone beam data corresponding to each of the respective subportions of the portion to be imaged. The program would further include a module for combining the cone beam data of each subportion to provide the complete data set corresponding to the portion of interest to be imaged.

Although various specific constructions have been given for the present invention, it is to be understood that these are for illustrative purposes only. Various modifications and adaptations will be readily apparent to those of skill in the art. For example, although the present invention has been described with reference to a scan trajectory having upper and lower circular scan paths, other alternatives are possible. For example, a helical path which encloses the portion to be imaged may be conveniently defined as the scan trajectory. In this case, the first, second and third regions can be suitably identified to retain the cone beam data being generated using such helical path. In view of these and other modifications, the scope of the present invention should be determined by reference to the claims appended hereto.

What is claimed is:

1. A method of pre-processing cone beam projection data for reconstructing substantially free of interpolation induced artifacts a three-dimensional (3D) image of a portion of an object using an inverse Radon transformation, said method comprising the steps of:

providing a mutually spaced cone beam irradiating source and a surface array radiation detector in fixed relationship to one another;

providing an object between said source and said detector;

irradiating at least said portion of said object within a field of view of said source;

moving both said source and detector relative to said object for scanning around said portion along a scan trajectory enclosing upper and lower extents of said portion by respective upper and lower scan paths joined therebetween by a predetermined connecting path;

identifying a first region on said surface array detector as a cone beam projection of said object bounded between respective similar projections of said upper and lower scan paths;

identifying second and third regions on said surface array detector respectively situated about said upper and lower scan path projections, each of said second and third regions respectively extending sufficiently beyond said first region to provide a predetermined additional cone beam projection of said object;

detecting cone beam projection data at said surface array detector for a plurality of scan positions along said scan trajectory;

retaining cone beam projection data acquired within said first, second and third regions; and processing said retained data to reconstruct substantially free of interpolation induced artifacts a 3D image of said portion by said inverse Radon transformation.

2. A method in accordance with claim 1 wherein said second region is situated adjacent to said upper scan path projection.

3. A method in accordance with claim 1 wherein said third region is situated adjacent to said lower scan path projection.

4. A method in accordance with claim 1 wherein each of said second and third regions is respectively situated adjacent to said upper and lower scan path projections.

5. A method in accordance with claim 1 wherein said second region shares a mutually intersecting subregion with said first region.

6. A method in accordance with claim 1 wherein said third region shares a mutually intersecting subregion with said first region.

7. A method in accordance with claim 1 wherein each respective one of said second and third regions shares a respective mutually intersecting subregion with said first region.

8. A method in accordance with claim 1 wherein said surface array detector comprises a planar surface.

9. A method in accordance with claim 1 which comprises moving said source along said scan trajectory in a continuous scan.

10. A method in accordance with claim 1 which comprises moving said source along said scan trajectory in a stepwise scan.

11. A method in accordance with claim 1 wherein a complete set of Radon data is acquired for reconstructing substantially free of interpolation induced artifacts an exact 3D image of said portion.

12. A system for pre-processing cone beam projection data to reconstruct substantially free of interpolation induced artifacts a three-dimensional (3D) image of a portion of an object, said system comprising:

a cone beam source for irradiating at least said portion of said object;

a surface array radiation detector positioned in fixed relationship with reference to said source to receive radiation from said source;

a scanning device causing relative motion of said source and object such that said source moves along a scan trajectory relative to said portion of said object, said device including means for scanning along upper and lower scan paths of said trajectory respectively enclosing upper and lower extents of said portion of said object and a connecting scan path therebetween;

means for identifying a first region on said surface array detector as a cone beam projection of said object bounded between respective similar projections of said upper and lower scan paths;

means for identifying second and third regions on said surface array detector respectively situated about said upper and lower scan path projections and wherein each of said second and third regions extends sufficiently beyond said first region to provide a predetermined additional cone beam projection of said object;

means for acquiring cone beam projection data at said surface detector for a plurality of source positions along said scan trajectory;

means for retaining cone beam projection data acquired within said first, second and third regions; and means for processing said retained data into a 3D image of said portion by a Radon inverse transformation, said image being substantially free of interpolation induced artifacts.

13. A system in accordance with claim 12 wherein said second region is situated adjacent to said upper scan path projection.

14. A system in accordance with claim 12 wherein said third region is situated adjacent to said lower scan path projection.

15. A system in accordance with claim 12 wherein each of said second and third regions is respectively situated adjacent to said upper and lower scan path projections.

16. A system in accordance with claim 12 wherein said second region shares a mutually intersecting subregion with said first region.

17. A system in accordance with claim 12 wherein said third region shares a mutually intersecting subregion with said first region.

18. A system in accordance with claim 12 wherein each respective one of said second and third regions shares a respective mutually intersecting subregion with said first region.

19. A system in accordance with claim 12 wherein said surface array radiation detector is a planar surface array radiation detector.

20. A system in accordance with claim 12 wherein said scanning device is adapted to move said source along said scan trajectory in a step-wise scan.

21. A system in accordance with claim 12 wherein said scanning device is adapted to move said source along said scan trajectory in a continuous scan.

22. A system in accordance with claim 12 further comprising a display connected to said processing means to display said image of said portion.

* * * * *